(12) United States Patent
Campbell et al.

(10) Patent No.: US 10,012,594 B2
(45) Date of Patent: Jul. 3, 2018

(54) COLIPHAGE BIOSENSOR

(71) Applicants: James K. Campbell, North Liberty, IN (US); Lyuda Trokhina, Goshen, IN (US)

(72) Inventors: James K. Campbell, North Liberty, IN (US); Lyuda Trokhina, Goshen, IN (US)

( * ) Notice: Subject to any disclaimer, the term of this patent is extended or adjusted under 35 U.S.C. 154(b) by 70 days.

(21) Appl. No.: 14/929,600

(22) Filed: Nov. 2, 2015

(65) Prior Publication Data
US 2016/0131591 A1 May 12, 2016

Related U.S. Application Data

(60) Provisional application No. 62/073,062, filed on Oct. 31, 2014.

(51) Int. Cl.
| | |
|---|---|
| *C12N 1/20* | (2006.01) |
| *G01N 21/78* | (2006.01) |
| *C12Q 1/04* | (2006.01) |
| *G01N 33/18* | (2006.01) |
| *G01N 31/22* | (2006.01) |

(52) U.S. Cl.
CPC ............ *G01N 21/78* (2013.01); *C12Q 1/04* (2013.01); *G01N 33/1826* (2013.01); *G01N 31/22* (2013.01)

(58) Field of Classification Search
None
See application file for complete search history.

(56) References Cited

U.S. PATENT DOCUMENTS

| | | | | |
|---|---|---|---|---|
| 4,956,274 A | * | 9/1990 | Khanna | C12Q 1/34 435/18 |
| 7,892,811 B2 | * | 2/2011 | Jia | C12N 1/06 435/173.7 |
| 2009/0298051 A1 | | 12/2009 | Salter et al. | |
| 2011/0112503 A1 | * | 5/2011 | Ismagilov | B01L 3/502715 604/500 |

OTHER PUBLICATIONS

Langley et al. Molecular basis of beta-galactosidase alpha-complementation.Proc Natl Acad Sci U S A. Apr. 1975;72(4):1254-7.*
"Part 9000 Microbiological Examination," Standards for the Examination of Water and Wastewater, Americal Public Health Associate, 1999, 46 pgs.
"Review of Coliphages as Possible Indicators of Fecal Contamination for Ambient Water Quality," Pub. 820-R-15-098, EPA Office of Water, Apr. 17, 2015, 129 pgs.
Berg et al., "Validity of Fecal Coliforms, Total Coliforms, and Fecal *Streptococci* as Indicators of Viruses in Chlorinated Primary Sewage Effluents," Applied and Environmental Microbiology, Dec. 1978, vol. 36, No. 6, pp. 880-884.
Havelaar et al., "F-Specific RNA Bacteriophages are Adequate Model Organisms for Enteric Viruses in Fresh Water," Applied and Evironmental Microbiology, Sep. 1998, vol. 59, No. 9, pp. 2956-2962.
Ijzerman et al., "Development and Evaluation of a Colorimetric Coliphage Assay Detection System," Virginia Water Resources Research Center, Bulletin 183, Virginia Polytechnic Institute and State University, Mar. 1994, 35 pgs.
Marino et al., "Applicability of the Recreational Water Quality Standard Guidelines," Wat. Sci. Tech., vol. 31, No. 5-6, pp. 27-31, 1995.
Stanek et al., "Rapid coliphaage detection assay," Journal of Virological Methods 91 (2001) pp. 93-98.
Stetler, Coliphages as Indicators of Enteroviruses, Applied and Environmental Microbiology, Sep. 1984, vol. 48, No. 3, pp. 668-670.

* cited by examiner

*Primary Examiner* — Michelle S Horning
(74) *Attorney, Agent, or Firm* — Woodward, Emhardt, Moriarty, McNett & Henry LLP

(57) ABSTRACT

Disclosed are methods, apparatuses, and genetically modified bacteria that may be used to detect bacteriophages in a sample. In some embodiments, a rapid detection test is disclosed to test for the presence of coliphages which may indicate the presence of human or animal waste contamination in water samples.

18 Claims, 22 Drawing Sheets

Figure 17

SEQ ID NO 1:

>BBa_K1477014 Part-only sequence (432 bp)
ttgacagctagctcactcctagctactgtgctagctactagagaaagaagaagaaatactagatgaccatgattacggattcactggccgtcgttttacaa
cgtcgtgactgggaaaaccctggcgttacccaacttaatcgccttgcagcacatccccctttcgccagctggcgtaatagcgaagaggcccgcaccgatc
gcccttcccaacagttgcgcagcctgaatggcgaatggcgctttgcctggtttccggcaccagaagcggtgccggaaagctggctggagtaataatacta
gagccaggcatcaaataaaacgaaaggctcagtcgaaagactgggcctttcgttttatctgttgtttgtcggtgaacgctctctactagagtcacactgg
ctcaccttcgggtgggcctttctgcgtttata

Figure 18

SEQ ID NO 2:

>BBa_K1477030 Part-only sequence (568 bp)
taatacgactcactatagggaatacaagctacttgttctttttgcatactagagatacttaggaggtattatgaatatatttgaaatgttacgtatagat
gaaggtcttagacttaaaatctataaagacacagaaggctattacactattggcatcggtcatttgcttacaaaaagtccatcacttaatgctgctaaat
ctgaattagataaagctattgggcgtaattgcaatggtgtaattacaaaagatgaggctgaaaaactctttaatcaggatgttgatgctgctgttcgcgg
aatcctgagaaatgctaaattaaaaacggtttatgattctcttgatgcggttcgtcgctgtgcattgattaatatggttttccaaatgggagaaaccggt
gtggcaggatttactaactctttacgtatgcttcaacaaaaacgctgggatgaagcagcagttaacttagctaaaagtagatggtataatcaaacaccta
atcgcgcaaaacgagtcattacaacgtttagaactggcacttgggacgcgtataaaaatctataaagc

COLIPHAGE BIOSENSOR

REFERENCE TO RELATED APPLICATIONS

This application claims the benefit of priority to U.S. Provisional Patent Application No. 62/073,062 filed on Oct. 31, 2014.

BACKGROUND

Ingesting water contaminated by human and/or animal waste is a serious problem, both inside of the United States as well as globally. Diseases caused by parasites such as cryptosporidium, amoeba, as well as enteric viruses such as hepatitis virus or norovirus can be transmitted by water contaminated by human and/or animal waste.

Disease symptoms from waterborne contaminants can include gastroenteritis, dysentery, acute fever and may lead to hospitalization or even death.

Fecal contamination of water is often determined by detecting common bacteria from the intestines of humans and animals called "coliforms." *Escherichia coli* (*E. coli*) is the most common coliform. The most specific test for contamination of water by human or animal fecal matter is an overnight test for the growth of *E. coli* on special growth media.

Given this background, there remains a need for tests which detect coliforms.

SUMMARY

In some aspects, the present disclosure relates to a test for bacteriophage in a sample. Such bacteriophage include, but are not limited to bacteriophage that infect coliforms called coliphage.

In other aspects, the present disclosure relates to a rapid colorimetric test for bacteriophage in a sample.

In still other aspects, the present disclosure relates to genetically modified microorganisms that may be used in apparatuses or biosensors for bacteriophage in a sample.

Additional embodiments of the invention, as well as features and advantages thereof, will be apparent from the descriptions herein.

BRIEF DESCRIPTION OF THE DRAWINGS

FIG. 17 shows SEQ ID NO 1, a part of the plasmid designated BBa_K1477014 which is registered with the iGEM registry.

FIG. 18 shows SEQ ID NO 2, a part of the plasmid designated BBa_K1477030 which is registered with the iGEM registry.

DETAILED DESCRIPTION

Figure 1:
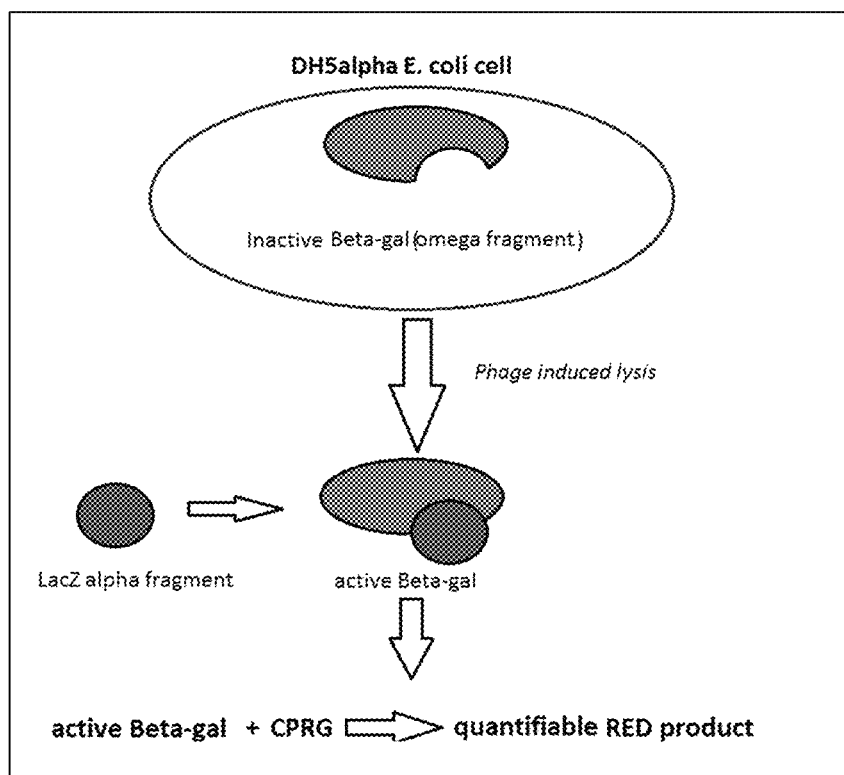
FIG. 1 shows a flow diagram of one embodiment of the present disclosure.

For the purposes of promoting an understanding of the principles of the invention, reference will now be made to certain embodiments and specific language will be used to describe the same. It will nevertheless be understood that no limitation of the scope of the invention is thereby intended, such alterations and further modifications, and such further applications of the principles of the invention as described herein being contemplated as would normally occur to one skilled in the art to which the invention relates.

As discussed above, aspects of the present disclosure relate to compositions, systems, apparatuses, and/or methods for detecting contaminants in a sample.

As used in this specification, and unless otherwise indicated, the term "bacteriophage" means a virus that infects and/or replicates within a bacterium. "Coliphage" means a type of bacteriophage that infects *Escherichia coli* ("*E. coli*") bacteria.

ß-galactosidase is a hydrolase enzyme that catalyzes the hydrolysis of ß-galactosides. In *E. coli* bacteria, the gene that encodes for ß-galactosidase resides in the lac operon which is an inducible system that is activated in the presence of lactose when the level of glucose in low. In *E. coli*, ß-galactosidase is formed from two peptide fragments, called LacZα and LacZΩ, which assemble into a functional enzyme. However, neither peptide is active on its own.

Chlorophenol red-ß-D-galactopyranoside ("CPRG") is a colorimetric indicator that comprises a ß-galactoside and an indicator that is hydrolyzed in the presence of ß-galactosidase. When hydrolyzed, CPRG turns from a lemon yellow color to a deep purplish red. Such a color change can be observed by the human eye, or may also be detected using a spectrophotometer. When a spectrophotometer is used in embodiments of the present disclosure, any suitable wavelengths of light may be used to detect absorbance and/or transmittance, including but not limited to wavelengths of light in the range of about 700 nanometers (nm) to about 500 nm. In some preferred embodiments, wavelengths of 560 nm and/or 572 nm are used to measure absorbance and/or transmittance.

Where possible, procedures and/or sequences were identified using the International Genetically Engineered Machine (iGEM) registry and website. The iGEM website is located at http://igem.org. When registry numbers are disclosed herein, reference is made to iGEM's Registry of Standard Parts, located at http://parts.igem.org. Additionally, iGEM provides procedures, protocols, and/or standards for working with these standard biologic parts. In particular, iGEM standard RFC[10] also called "BioBricks Foundation: BBFRFC10", which may be found at http://igem.org is hereby incorporated by reference in its entirety.

As used by iGEM and herein, "parts" means a sequence of DNA is compatible with an assembly standard, as long as its sequence meets the requirements of said standard; this means that the part does not have any restriction sites that would interfere with the assembly. "Assembly" means combining two part samples together in series to form a new composite part. Traditional assembly is done through the use of restriction sites (cutting and ligating) as defined by the assembly standard. Assembly is facilitated through assembly standards. "Plasmid backbone" means a plasmid that propagates a sample of a part, located in between the prefix and suffix of the plasmid backbone. Therefore the plasmid backbone will define the assembly standard for the part it maintains.

While many of the parts may be obtainable from or through iGEM, some may not. In such cases, information by be retrieved from the National Center for Biotechnology Information (NCBI) at the National Institutes of Health (NIH) and their website located at http://www.ncbi.nlm.nih.gov.

In some embodiments of the present disclosure, an apparatus for detecting bacteriophage is disclosed. In some particular embodiments, the bacteriophages being detected are coliphages.

Genetically modified bacteria may be used in embodiments of the present disclosure. For example, genetically modified *E. coli* bacteria are prepared by inserting into the bacteria a plasmid that encodes for expression or overexpression of the LacZΩ fragment of ß-galactosidase. The bacteria may also be genetically modified to express or overexpress endolysin production. When endolysin is expressed or overexpressed, this may shut off or otherwise make the lysogenic cycle of the cell inactive and promote cell lysis when infected with a bacteriophage. When cell lysis occurs under these conditions, lysis often occurs more rapidly than would otherwise be observed in the non-genetically modified bacteria. This rapid lysis helps to reduce the analysis time in embodiments of the present disclosure. Additionally, and/or alternatively, cells, including but not limited to prokaryotic or eukaryotic cells may be used in certain embodiments. In some preferred embodiments, the eukaryotic cells that are used may be mammalian cells. Preparation of genetically modified cells may be carried out by procedures known to those of ordinary skill in the art.

When a genetically modified cell or bacteria that expresses or overexpresses the LacZΩ fragment of ß-galactosidase and is infected with a bacteriophage, lysis occurs spilling the LacZΩ fragment of ß-galactosidase. When the LacZα fragment of ß-galactosidase is present, the LacZΩ and LacZα fragments assemble to form an active ß-galactosidase protein. Once formed, the active ß-galactosidase hydrolyses the glyosidic linkage of CPRG, and a color change may be observed.

Referring now to the figures, FIG. 1 shows one embodiment of the present disclosure where DH5alpha *E. coli* cells were genetically modified to express the LacZΩ fragment of ß-galactosidase. When such a cell is lysed by a bacteriophage induced lysis, the LacZΩ fragment of ß-galactosidase is released. The LacZα fragment of ß-galactosidase is present as previously isolated and provided. When the LacZΩ fragment of ß-galactosidase assembles with a LacZα fragment of ß-galactosidase present an active ß-galactosidase protein is formed. When the active ß-galactosidase protein hydrolyses the glyosidic linkage of CPRG, and a color change may be observed indicating presence of a bacteriophage.

Figure 2:
FIG. 2 shows a digital image of the materials including enzymes and lab equipment used for electroporation procedures to ligate parts BBa_K1477030 and BBa_K1477014 into a plasmid backbone to genetically modify bacteria.

FIG. 2 shows a digital image of the materials including enzymes and lab equipment used for electroporation procedures to ligate parts BBa_K1477030 and BBa_K1477014 into a plasmid backbone to genetically modify bacteria.

Figure 3:
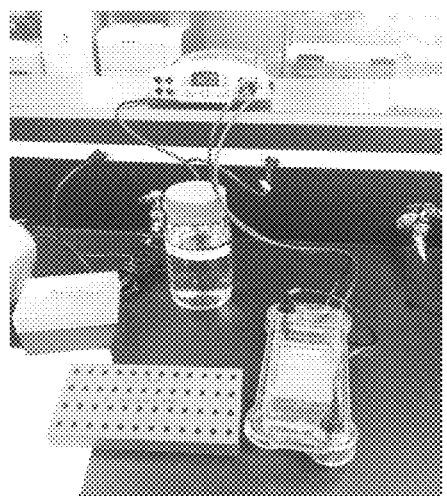
FIG. 3 shows a digital image of a gel electrophoresis experimental setup.

FIG. 3 shows a digital image of a gel electrophoresis experimental setup which may be used to separate, purify, and/or quantify the length of DNA parts.

Figure 4:
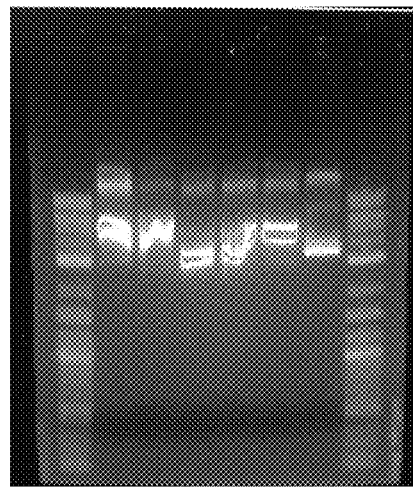
FIG. 4 shows a digital image of a representative gel electrophoresis gel separating DNA sequences of various lengths.

FIG. 4 a digital image of a representative gel electrophoresis gel separating DNA sequences of various lengths.

Figure 5:
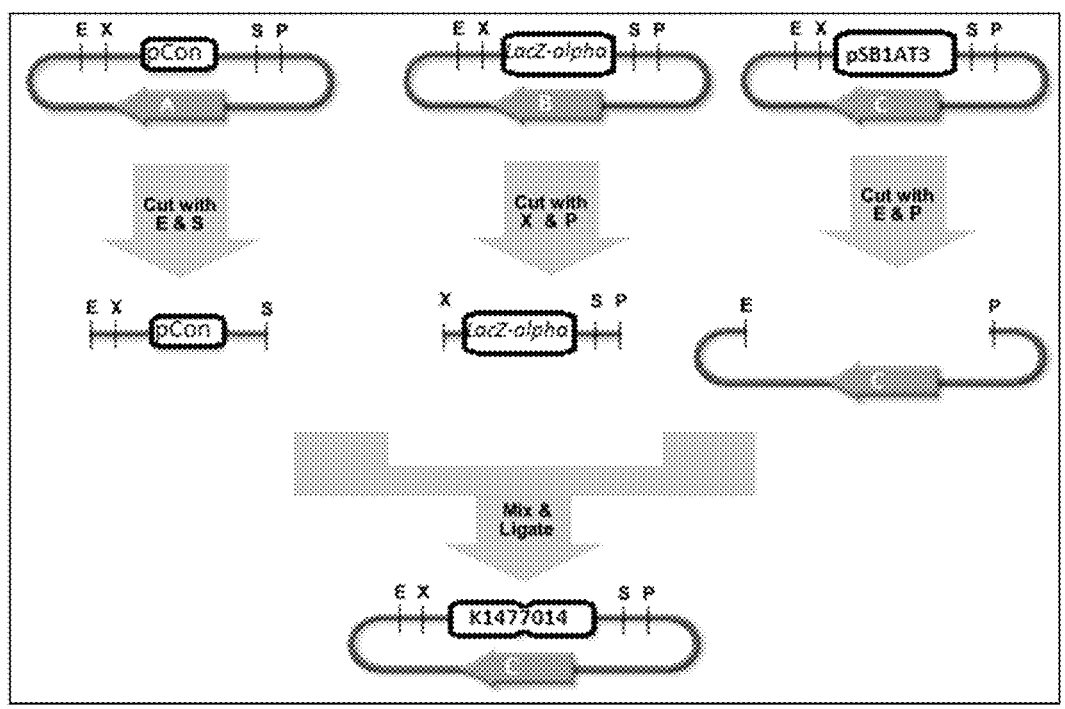
FIG. 5 shows a flow diagram for the preparation of one plasmid used in embodiments of the present disclosure.

FIG. 5 shows a flow diagram for the preparation of one plasmid used in embodiments of the present disclosure. The plasmid shown in this figure is used to impart a promoter and encoding for a LacZα fragment of ß-galactosidase to be produced, isolated, and/or purified for use in embodiments of the present invention. The LacZα fragment is provided outside of the cell so that when a cell infected with a bacteriophage lyses and releases a LacZΩ fragment, an active ß-galactosidase protein is formed, and subsequently, the active ß-galactosidase protein is formed may hydrolyze CPRG to indicate presence of a bacteriophage in the sample.

Figure 6:
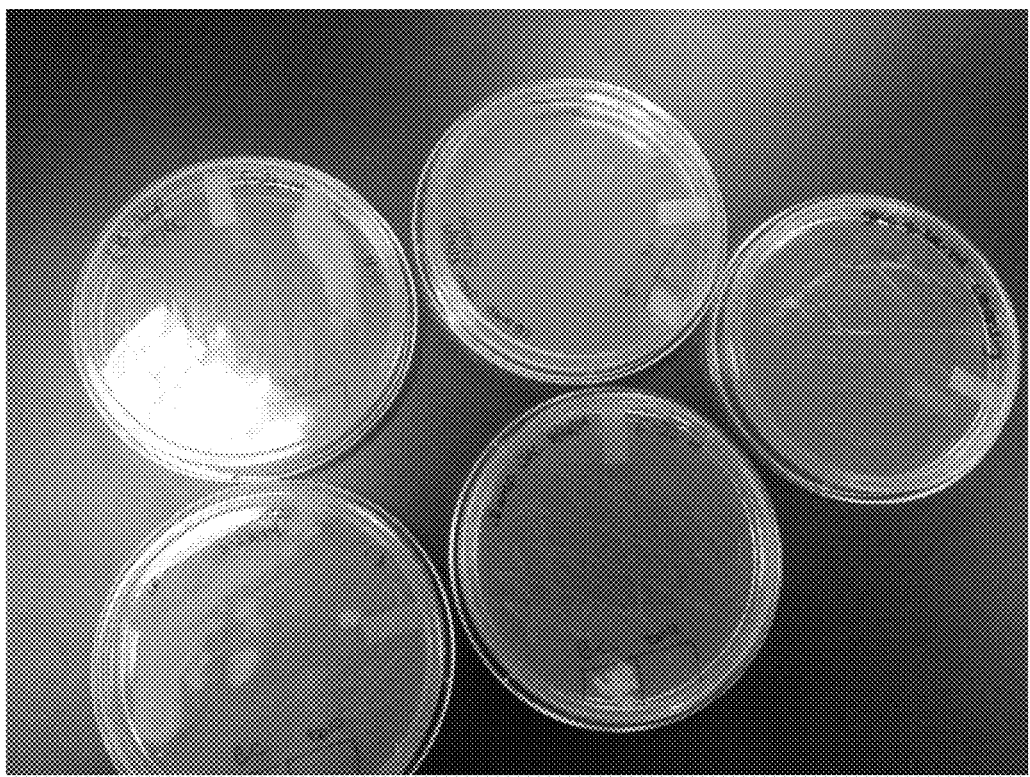
FIG. 6 shows a digital image of cell culture plates with red bacterial colonies indicating successful ligation of a constitutive promoter with a red fluorescent protein.

FIG. 6 shows a digital image of cell culture plates with red bacterial colonies indicating successful ligation of a constitutive promoter with a red fluorescent protein which was used to test the assembly and growing protocols used in embodiments of the present disclosure.

Figure 7:
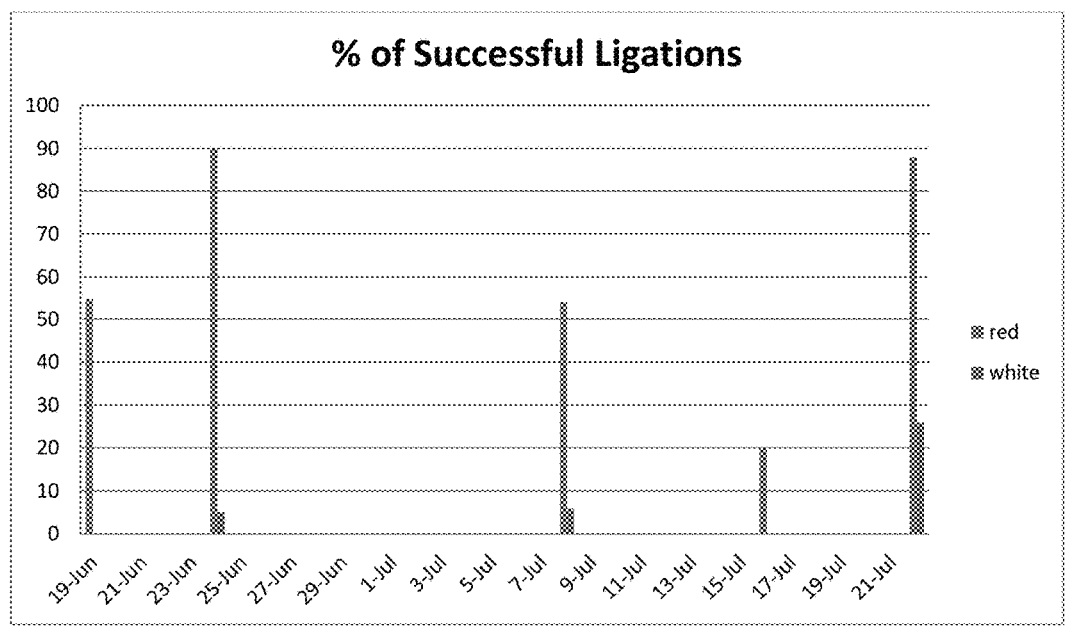
FIG. 7 shows the number of successful ligation experiments performed on certain days.

FIG. 7 shows the number of successful ligation experiments performed on certain days.

Figure 8:
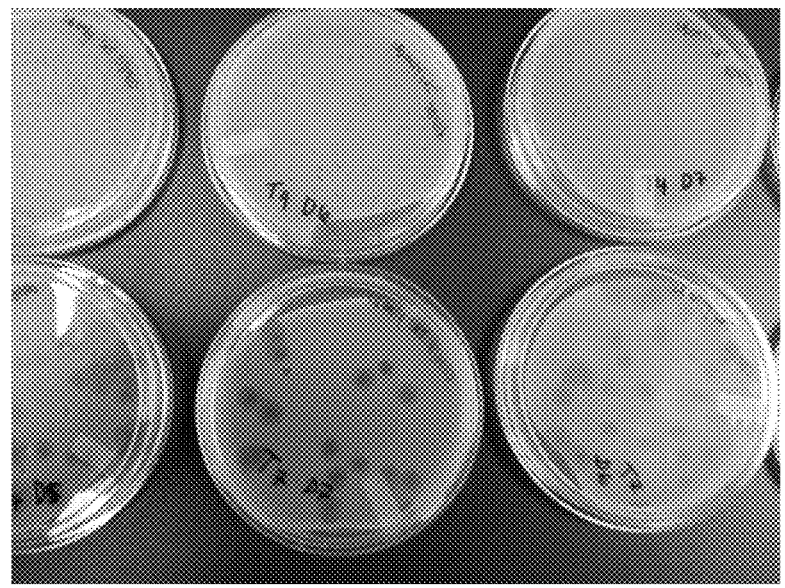
FIG. 8 shows a digital image of cell culture plates with logarithmic concentrations of viruses which was used to determine the variations of color change in chlorophenol red-ß-D-galactopyranoside.

FIG. 8 shows a digital image of cell culture plates with logarithmic concentrations of viruses which was used to determine the variations of color change in chlorophenol red-ß-D-galactopyranoside.

Figure 9:
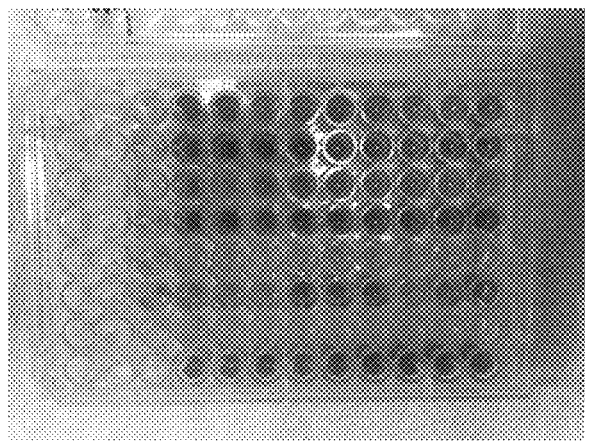
FIG. 9 shows a digital image of a multi-cell plate with chlorophenol red-ß-D-galactopyranoside colorimetric indicator as it changes color from a lemon yellow to a deep purplish red.

FIG. 9 shows a digital image of a multi-cell plate with chlorophenol red-ß-D-galactopyranoside colorimetric indicator as it changes color from a lemon yellow to a deep purplish red.

Figure 10:
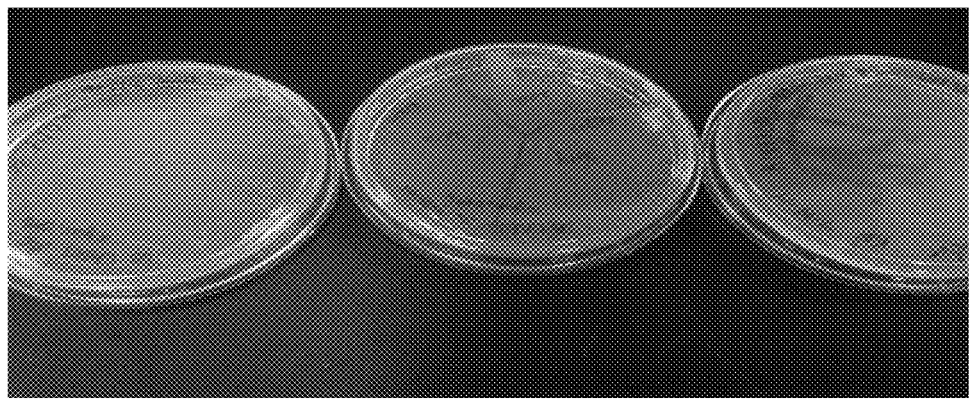
FIG. 10 shows a digital image of cell culture plates used to perform a blue/white screening experiment for the presence of ß-galactosidase.

FIG. 10 shows a digital image of cell culture plates used to perform a blue/white screening experiment for the presence of ß-galactosidase which was used to the assembly and growing protocols used in embodiments of the present disclosure.

Figure 11:
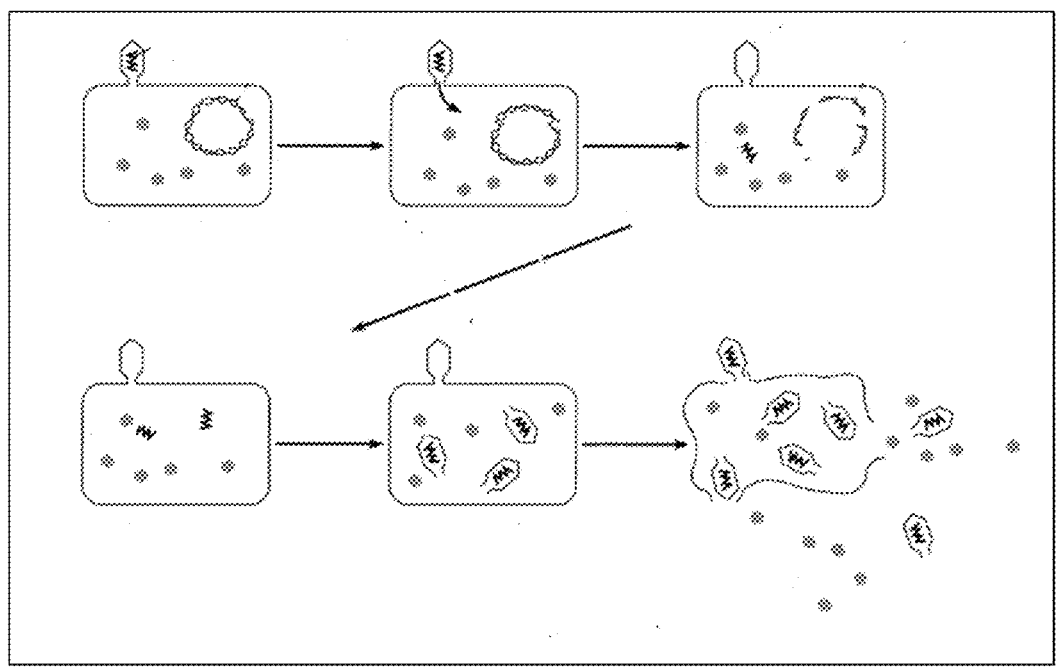
FIG. 11 shows a drawing of the life cycle of a virus in a cell modified with a plasmid coding for the production of LacZΩ fragment of ß-galactosidase.

FIG. 11 shows a drawing of the life cycle of a virus in a cell modified with a plasmid coding for the production of LacZΩ fragment of ß-galactosidase. In this drawing, the plasmid does not comprise a endolysin terminator. Both the lytic cycle as well as lysogenic are likely operating in this embodiment, and a longer incubation period is required for the virus to reproduce. This is in contrast to the embodiment shown in FIG. 14 and described below.

Figure 12:
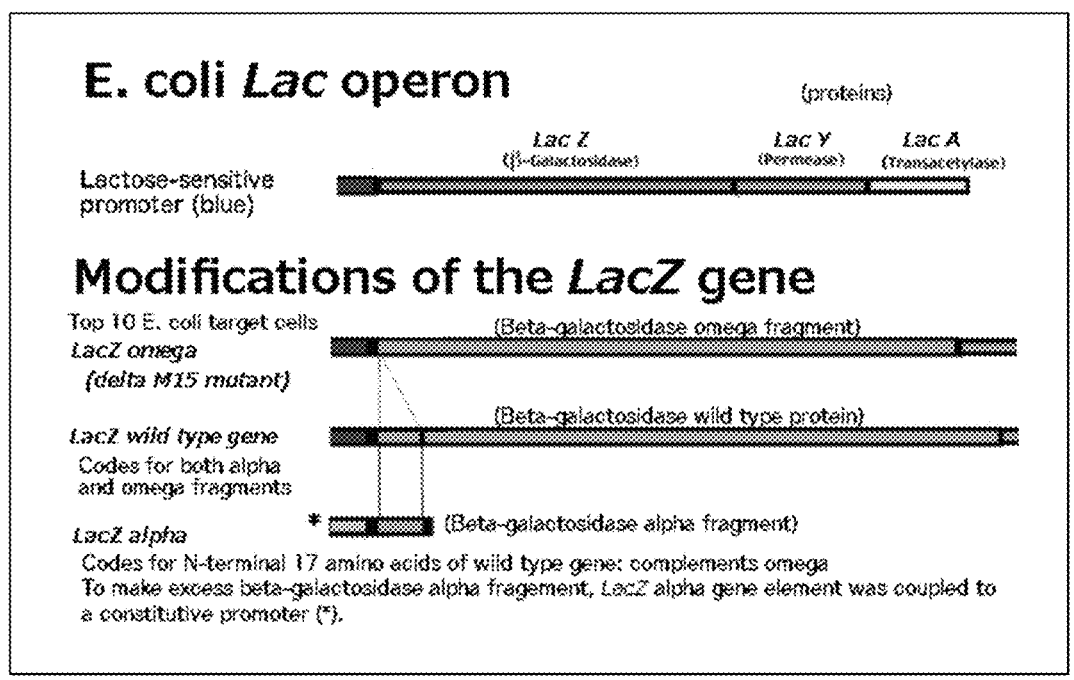
FIG. 12 shows modifications made to the LacZ gene in *E. coli*.

FIG. 12 shows a drawing of the modifications made to the LacZ gene of *E. coli*. To produce more LacZα fragment, a constitutive promoter was coupled to the LacZα as well as other modifications to ensure that only the LacZα fragment was produced.

Figure 13:
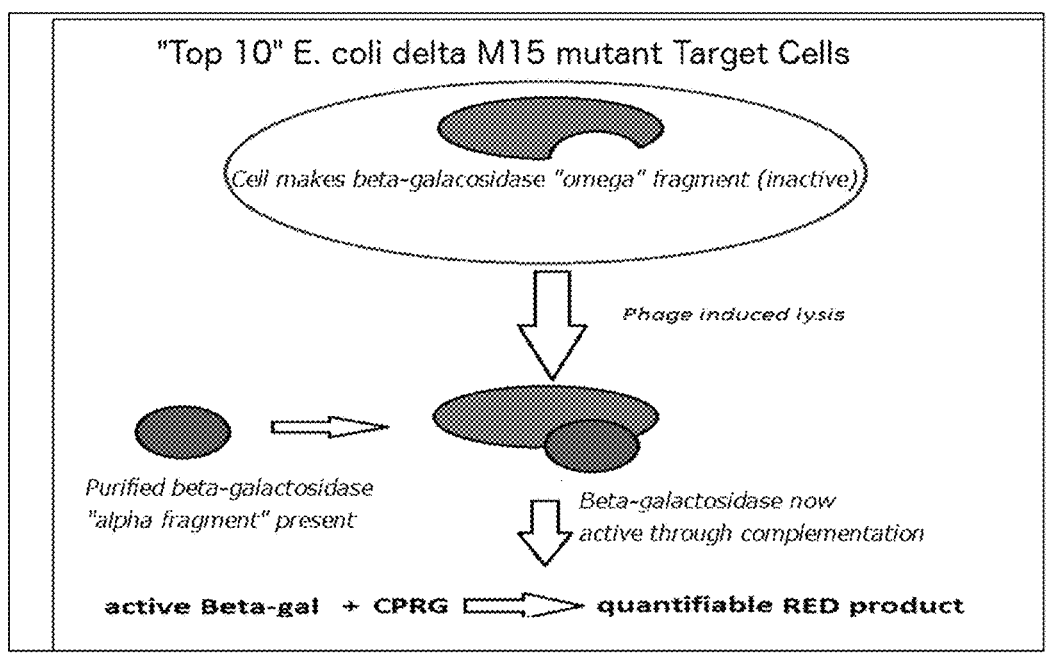
FIG. 13 shows a flow diagram of one embodiment of the present disclosure.

FIG. 13 shows one embodiment of the present disclosure where the *E. coli* bacteria used were called "TOP10" delta M15 genotype manufactured by Invitrogen™ and purchased from the iGEM registry.

Figure 14:
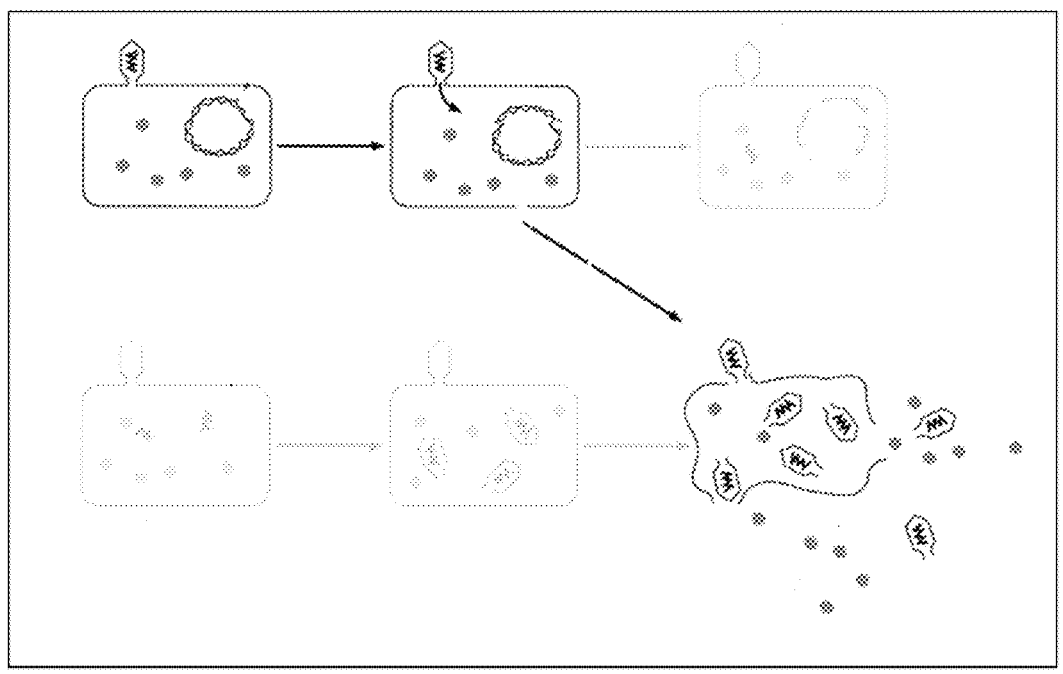
FIG. 14 shows show a flow diagram of the modified life cycle of a virus when a plasmid comprising endolysin terminator is introduced. This may cause the cell to lyse by bypassing the lysogenic cycle of the cell.

FIG. 14 shows a flow diagram of the modified life cycle of a virus when a plasmid comprising endolysin terminator is introduced. This may cause the cell to lyse by bypassing the lysogenic cycle of the cell.

Figure 15:
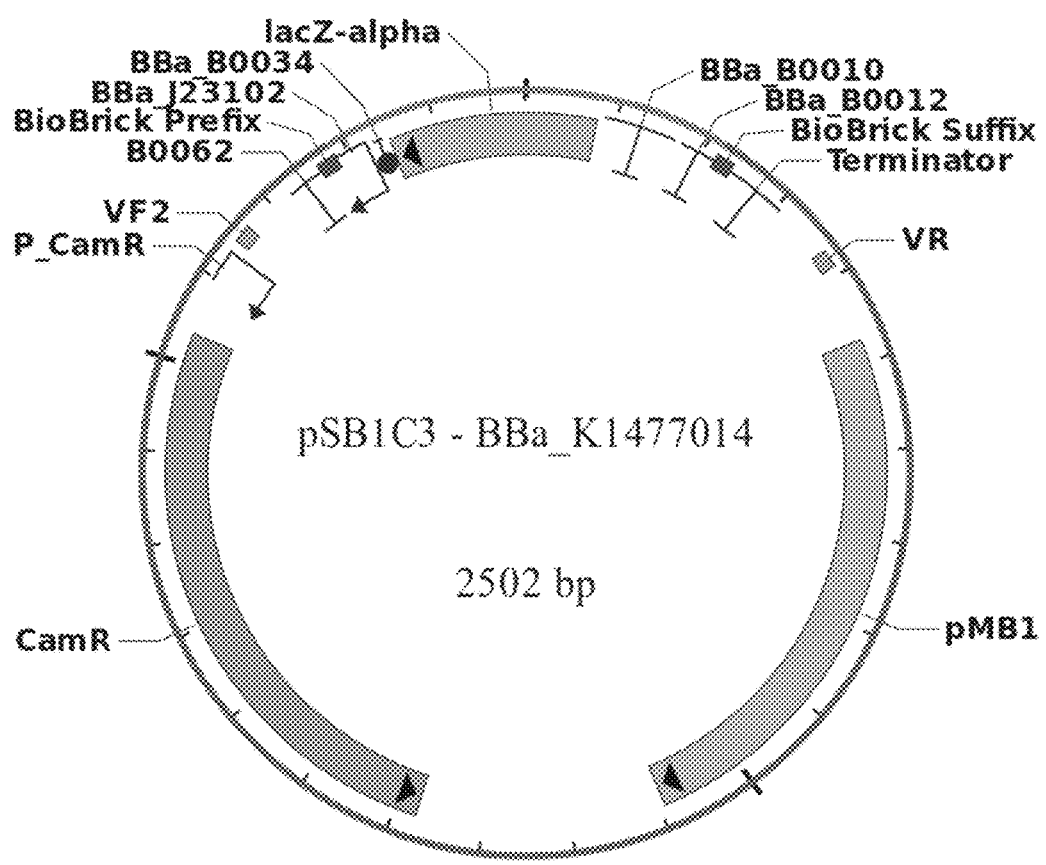
FIG. 15 shows a plasmid, designated BBa_K1477014 registered with the iGEM registry, comprising a constitutive promoter and a gene that codes for the LacZα protein fragment.

FIG. 15 shows a plasmid, designated BBa_K1477014 registered with the iGEM registry, comprising a constitutive promoter and a gene that codes for the LacZα protein fragment. This plasmid may be used as a source for the LacZα part and incorporated into a plasmid to be incorporated into a microorganism using the standard procedures and protocols from iGEM.

Figure 16:
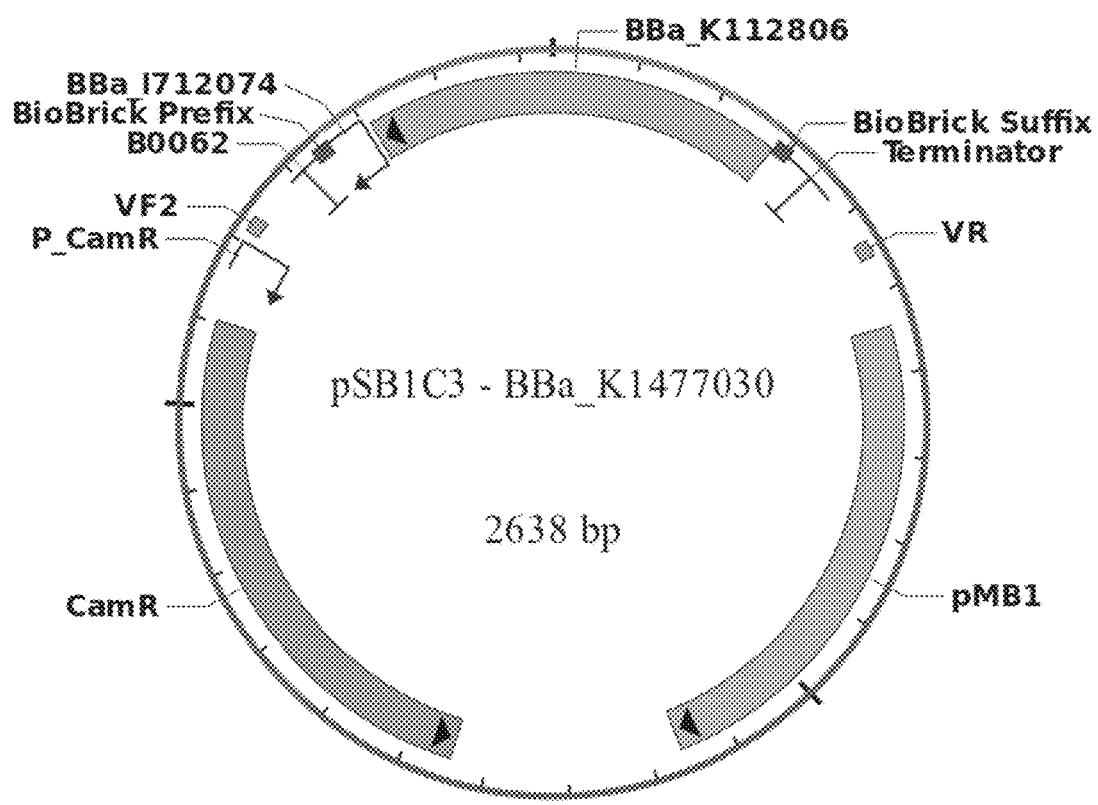
FIG. 16 shows a plasmid, designated BBa_K1477030 registered with the iGEM registry, comprising a gene that codes for the LacZΩ protein fragment.

FIG. 16 shows a plasmid, designated BBa_K1477030 registered with the iGEM registry, comprising a gene that codes for the LacZΩ protein fragment. This plasmid may be used as a source for the LacZΩ part and incorporated into a plasmid to be incorporated into a microorganism using the standard procedures and protocols from iGEM.

FIG. 17 shows SEQ ID NO 1, a part of the plasmid designated BBa_K1477014 which is registered with the iGEM registry and may be incorporated into plasmid to be incorporated into a microorganism using the standard procedures and protocols from iGEM.

FIG. 18 shows SEQ ID NO 2, a part of the plasmid designated BBa_K1477030 which is registered with the iGEM registry and may be incorporated into plasmid to be incorporated into a microorganism using the standard procedures and protocols from iGEM.

Figure 19:
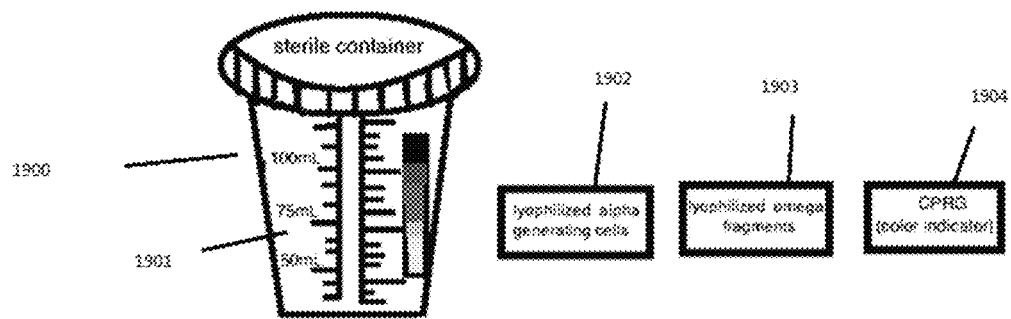
FIG. 19 shows one embodiment of an article of manufacture or test kit comprising a sterile container, lyophilized alpha generating cells, lyophilized omega fragments, and/or CPRG or other color indicator.
Figure 20:
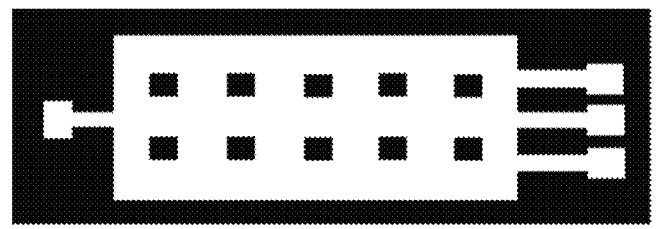
FIG. 20 shows a master mold with a patterned wafer.
Figure 21:
FIG. 21 shows a PDMS microfluiclic structure made from the master mold of the patterned wafer. Picture taken after PDMS cast was pulled off (you can see some areas of SU-8 got peeled up). The third inlet channel was lost after development.
Figure 22:
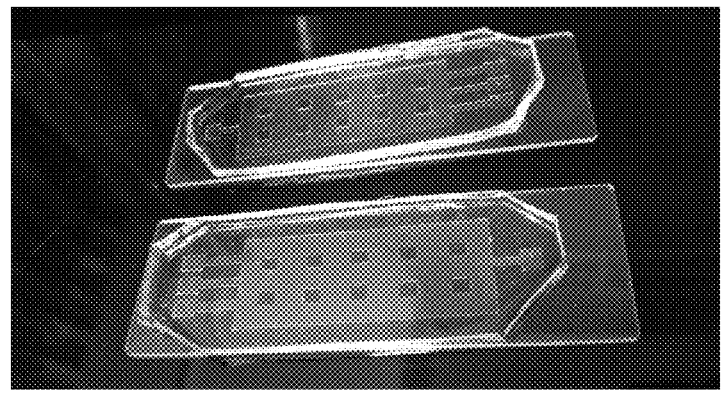
FIG. 22 shows a glass bonded PDMS device with dye. Fluid flowed easily!

FIG. 19 shows one embodiment of a of an article of manufacture or test kit (1900) comprising a sterile container (1901), lyophilized alpha generating cells (1902), lyophilized omega fragments (1902), and/or CPRG or other color indicator (1903).

Example 1

Preparation/Manufacture of Substrate

A microfluidic device using negative lithography was made to create a patterned wafer and the pattern in the wafer was used as a negative master mold to create a PDMS microfluidic structure. The PDMS microfluidic structure will use the application of hydrostatic transport of a liquid media in methods and apparatuses of the present disclosure. The PDMS microfluidic structure was then adhered to a glass slide to create a sealed chamber and that will be used to transport liquids through microfluidic channels.

Microfluidics is a broad term that describes various applications through channels and networks in the micron region. A microfluidic channel is commonly defined as having one or more dimension less than 100 microns in size. Transport mechanisms used by microfluidics to transfer liquids may include capillary forces, hydrostatic pressure gradients, electrokinetics, pumps, magnetism and/or digital arrays. Microfluidic channel material is important to consider when choosing the transport mechanism.

A master mold with a patterned wafer was prepared, and the master mold was further used to create a PDMS microfluidic device and to transport liquids through the PDMS microfluidic device.

Materials and Methods:

A patterned wafer that will be used as a master mold was prepared. The wafer was cleaned with acetone, isopropanol, deionized water and dried with an air can. The wafer underwent a dehydration bake on a hot plate at 110° C. for three to four minutes to remove any residual liquids. A HMDS application was performed on the wafer to improve photoresist adhesion to the wafer substrate. HMDS was applied to the wafer by putting it into a sealed but non-vacuumed chamber with an open bottle of HDMS for 15 minutes. After removal from the chamber the wafer underwent another dehydration bake on a hot plate for 15 seconds at 110° C.

The wafer was then primed for photoresist application. The photoresist used was SU8-25 which was estimated to give a thickness of approximately 25 microns; In further experiments, we changed this to three times as much SU8-25 in attempts to make the final thickness between 75 and 80 microns. Room lights were turned off and special orange lights that filter out light below 530 nanometers were used because SU8-25 photoresist is sensitive to ultraviolet light. The SU8-25 photoresist was applied using a static spin. Each wafer was placed on a two inch chuck and a centering spin is done to ensure the wafer is centered. An eight milliliter pipette was used to apply the SU8-25 photoresist to the wafer. The pipette was used to cover the entire wafer with SU8-25 photoresist and to remove any air bubbles. The first step of the procedure was a 5 second dwell at 500 RPM with a ramp rate of 100 RPM per second. The second step of the recipe was a 40 second dwell at 1000 RPM.

A soft bake on a hot plate was performed on each wafer (after the photoresist was spun on) to remove any solvents and harden the photoresist. Each wafer's soft bake was started at 65° C. and after three minutes the hot plate temperature was raised to 95° C. for an additional seven minutes of baking. After the soft bake the wafer was completely covered and encased in tinfoil to ensure no UV light exposure during transport down to the nanotech lab.

Room lights in the nanotech lab were turned off and orange lights were again used to ensure no unintended UV exposure of the wafer as it was taken out of the tinfoil case. The wafer was inserted into a MJB3 apparatus for exposure. The mask was put onto the mask holder and was held onto the mask holder by vacuum. The mask holder slid into the machine chrome/dark side down. The mask holder was brought into hard contact with the wafer and was exposed to UV light for 60 seconds. The wafer was again encased in tinfoil for transport back up to the chemistry lab.

With chemistry lab lights off and orange lights on the wafer was taken out of the tinfoil case. A post exposure bake (PEB) on a hot plate was performed on the wafer to selectively cross-link and strengthen the exposed area of photoresist. The wafers' post exposure bake was started at 65° C. and after one minute the hot plate temperature was raised to 95° C. for an additional three minutes of baking. After PEB the wafer was developed by placing it in a bath of developer and gently swirled for five and one half minutes to develop the pattern in the wafer. The wafer was then removed from the bath, rinsed with isopropanol and air dried. The wafer was brought back down to the nanotech lab and images were taken of it with an optical microscope, profilometer readings were also taken and found to be 80,162 angstroms.

The second session of the lab was used to create a PDMS microfluidic structure from the master mold on one of the patterned wafer and to transfer liquids through the PDMS microfluidic structure. A PDMS mold was made with a 10:1 ratio of base to curing agent. The base and curing agent were weighed out in a plastic basin at approximately ten grams of base to one gram of curing agent, mixed together in and dropped up and down in the plastic basin to minimize bubble formation in the mixture. The mixture was poured onto the master mold/patterned wafer with a tinfoil barrier around it and bakes in an oven for about one hour and fifteen minutes at 95° C. While the PDMS on one of the patterned wafers was baking in the oven, the other patterned wafer had profilometer measurements taken on it. The scan length was 18 millimeters (mm), stylus force was 0.10 grams (g) and the speed was 0.40 mm pre sec. Height and widths were taken of the chamber, a single pillar and the three microfluidic channels.

After about an hour and fifteen minutes the PDMS on top of one of the patterned wafers was removed from the oven, the tinfoil was removed, excess tinfoil and PDMS were removed using a razor blade and the PDMS was gently removed from the patterned wafer. The PDMS was cut in half with scissors and both pieces were shaped to fit onto glass slides. Two glass slides were cleaned with isopropanol and air dried. The surface of the two glass slides' substrate and two PDMS pieces' channel side were activated using a corona generator for approximately five minutes. The two PDMS pieces were then applied channel side down to their own glass slide and allowed to bond for 30 minutes to form a PDMS microfluidic device.

While the two PDMS pieces and glass slides were bonding for 30 minutes there were attempts made to flow fluids through the two PDMS pieces that have bonded on glass slides overnight. Needles were used to poke holes on the top inlet of the overnight PDMS microfluidic devices and a needle was used to insert blue jean dye into bottom inlets of the overnight PDMS microfluidic devices and make the fluid flow through the microfluidic channels. When done bonding for 30 minutes, the same attempt is made to flow fluids through the 30 minute PDMS microfluidic devices using the same procedure used on the overnight PDMS microfluidic devices.

The uses of the terms "a" and "an" and "the" and similar references in the context of describing the invention (especially in the context of the following claims) are to be construed to cover both the singular and the plural unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and the foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. An apparatus for detecting bacteriophage comprising:
a substrate;
a genetically modified *Escherichia coli* bacterium;
a LacZα ß-galactosidase fragment; and
wherein said genetically modified *Escherichia coli* bacterium comprises a plasmid comprising SEQ ID NO 2.

2. An apparatus for detecting bacteriophage comprising:
a substrate;
a genetically modified *Escherichia coli* bacterium;
a LacZα ß-galactosidase fragment; and
wherein said genetically modified *Escherichia coli* bacterium comprises SEQ ID NO 2.

3. An apparatus for detecting bacteriophage comprising:
a genetically modified *Escherichia coli* bacterium;
wherein said genetically modified *Escherichia coli* bacterium comprises SEQ ID NO 1.

4. The apparatus for detecting bacteriophage of claim 3, wherein said genetically modified *Escherichia coli* bacterium comprises a plasmid comprising SEQ ID NO 1.

5. The apparatus for detecting bacteriophage of claim 3, further comprising a LacZα ß-galactosidase or a LacZΩ ß-galactosidase fragment.

6. The apparatus for detecting bacteriophage of claim 3, further comprising red-ß-D-galactopyranoside.

7. The apparatus for detecting bacteriophage of claim 1, further comprising red-ß-D-galactopyranoside.

8. The apparatus for detecting bacteriophage of claim 2, further comprising red-ß-D-galactopyranoside.

9. The apparatus for detecting bacteriophage of claim 1, wherein said genetically modified *Escherichia coli* bacterium is derived from the DH5alpha strain of *Escherichia coli*.

10. The apparatus for detecting bacteriophage of claim 2, wherein said genetically modified *Escherichia coli* bacterium is derived from the DH5alpha strain of *Escherichia coli*.

11. The apparatus for detecting bacteriophage of claim 3, wherein said genetically modified *Escherichia coli* bacterium is derived from the DH5alpha strain of *Escherichia coli*.

12. The apparatus for detecting bacteriophage of claim 3, further comprising a substrate.

13. The apparatus for detecting bacteriophage of claim 1, wherein said substrate comprises a microfluidic structure.

14. The apparatus for detecting bacteriophage of claim 2, wherein said substrate comprises a microfluidic structure.

15. The apparatus for detecting bacteriophage of claim 12, wherein said substrate comprises a microfluidic structure.

16. The apparatus for detecting bacteriophage of claim 1, wherein said substrate comprises a glass slide.

17. The apparatus for detecting bacteriophage of claim 2, wherein said substrate comprises a glass slide.

18. The apparatus for detecting bacteriophage of claim 12, wherein said substrate comprises a glass slide.

* * * * *

SEQUENCE LISTING

<160> NUMBER OF SEQ ID NOS: 2

<210> SEQ ID NO 1
<211> LENGTH: 432
<212> TYPE: DNA
<213> ORGANISM: Unknown
<220> FEATURE:
<223> OTHER INFORMATION: synthetic construct

<400> SEQUENCE: 1

```
ttgacagcta gctcagtcct aggtactgtg ctagctacta gagaaagagg agaaatacta      60
gatgaccatg attacggatt cactggccgt cgttttacaa cgtcgtgact gggaaaaccc     120
tggcgttacc caacttaatc gccttgcagc acatccccct ttcgccagct ggcgtaatag     180
cgaagaggcc cgcaccgatc gcccttccca acagttgcgc agcctgaatg gcgaatggcg     240
ctttgcctgg tttccggcac cagaagcggt gccggaaagc tggctggagt aataatacta     300
gagccaggca tcaaataaaa cgaaaggctc agtcgaaaga ctgggccttt cgttttatct     360
gttgtttgtc ggtgaacgct ctctactaga gtcacactgg ctcaccttcg ggtgggcctt     420
tctgcgttta ta                                                          432
```

-continued

```
<210> SEQ ID NO 2
<211> LENGTH: 568
<212> TYPE: DNA
<213> ORGANISM: Unknown
<220> FEATURE:
<223> OTHER INFORMATION: synthetic construct

<400> SEQUENCE: 2
taatacgact cactataggg aatacaagct acttgttctt tttgcatact agagatactt      60
aggaggtatt atgaatatat ttgaaatgtt acgtatagat gaaggtctta gacttaaaat    120
ctataaagac acagaaggct attacactat tggcatcggt catttgctta caaaaagtcc    180
atcacttaat gctgctaaat ctgaattaga taaagctatt gggcgtaatt gcaatggtgt    240
aattacaaaa gatgaggctg aaaaactctt taatcaggat gttgatgctg ctgttcgcgg    300
aatcctgaga aatgctaaat taaaaccggt ttatgattct cttgatgcgg ttcgtcgctg    360
tgcattgatt aatatggttt tccaaatggg agaaaccggt gtggcaggat ttactaactc    420
tttacgtatg cttcaacaaa aacgctggga tgaagcagca gttaacttag ctaaaagtag    480
atggtataat caaacaccta atcgcgcaaa acgagtcatt acaacgttta gaactggcac    540
ttgggacgcg tataaaaatc tataaagc                                       568
```